United States Patent [19]
Stilts, Jr.

[11] Patent Number: 5,247,928
[45] Date of Patent: Sep. 28, 1993

[54] THERAPEUTIC COLLAR

[76] Inventor: Jerry D. Stilts, Jr., 3911 Beckwith Rd., Mt. Juliet, Tenn. 37122

[21] Appl. No.: 950,490

[22] Filed: Sep. 25, 1992

Related U.S. Application Data

[63] Continuation of Ser. No. 678,799, Apr. 1, 1991, abandoned.

[51] Int. Cl.⁵ ................................................ A61F 7/10
[52] U.S. Cl. ...................................... 607/109; 607/114
[58] Field of Search .............................. 129/344–403, 129/379, 380; 62/530; 383/901; 2/60, 129

[56] References Cited

U.S. PATENT DOCUMENTS

| | | | |
|---|---|---|---|
| 1,473,506 | 11/1923 | Nessler | 128/402 |
| 2,562,121 | 7/1951 | Poux | 128/402 |
| 3,889,684 | 6/1975 | Lebold | 128/402 |
| 4,576,169 | 3/1986 | Williams | 128/402 |
| 4,641,655 | 2/1987 | Abt | 128/380 |
| 4,805,619 | 2/1989 | Swearingen | 128/402 |
| 4,832,030 | 5/1989 | DeCanto | 128/402 |
| 4,951,666 | 8/1990 | Imman et al. | 128/402 |

Primary Examiner—Mark S. Graham
Attorney, Agent, or Firm—Zarley, McKee, Thomte, Voorhees & Sease

[57] ABSTRACT

The therapeutic collar of this invention comprises an elongated flexible collar structure having opposite ends, upper and lower edges, and a centrally located inner compartment. The inner compartment has an access port therein. A moisture impervious flexible plastic container is located within the compartment, and has a closable access opening therein. A flap appears on the upper edge of the collar structure and normally extends over the access port in the collar structure. Attachment means are located on the ends of the collar structure to secure the ends of the collar structure together.

4 Claims, 1 Drawing Sheet

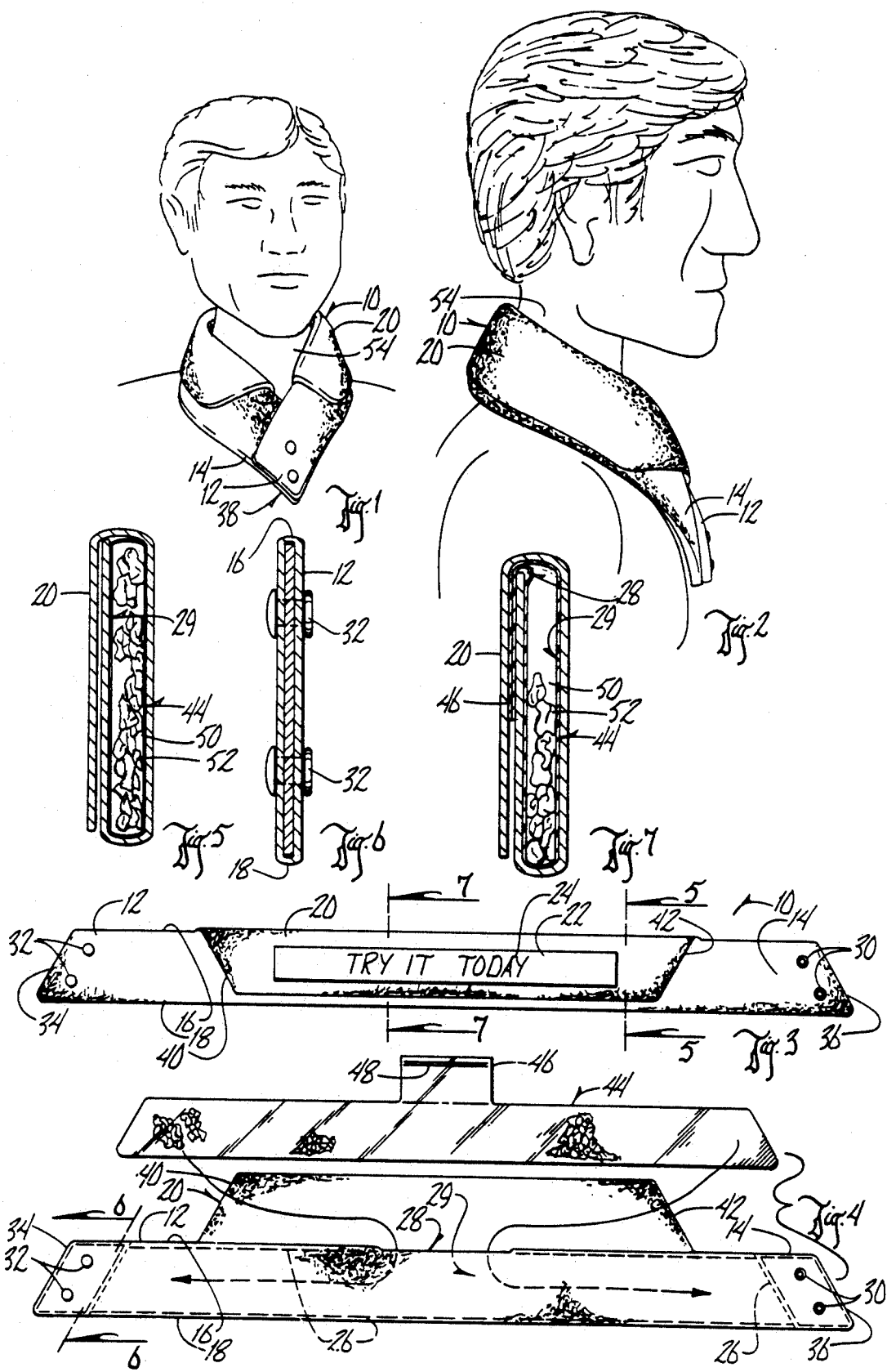

THERAPEUTIC COLLAR

This is a continuation of copending application Ser. No. 07/678,799 filed on Apr. 1, 1991, abandoned.

BACKGROUND OF THE INVENTION

Ice packs and hot water bottles are types of therapeutic devices which have existed for many years. They have been used to apply heat or cold to a person for only comfort purposes, i.e., to heat or cool the wearer, or to deal with pain reduction or healing if certain types of injuries or the like exist.

Ice-filled collars to cool a persons neck have previously existed. However, they often are uncomfortable to wear, and are often either difficult or messy to fill with ice or the like. Most such collars are unattractive, and do not lend themselves to style or the display of designs or messages which are common with sportswear attire.

It is therefore a principal object of this invention to provide a therapeutic collar which can easily be filled with a heating or coolant material, and which will prevent the material from leaking while the collar is being worn.

A further object of the invention is to provide a therapeutic collar which is comfortable to wear.

A further object of the invention is to provide a therapeutic collar which has an attractive design and which is aesthetically compatible with sportswear.

A further object of the invention is to provide a therapeutic dollar which has an appropriate exterior surface for fixing slogans, designs or the like.

A still further object of the invention is to provide a therapeutic collar which is economical of manufacture, durable in use, and refined in appearance.

These and other objects will be apparent to those skilled in the art.

SUMMARY OF THE INVENTION

The therapeutic collar of this invention comprises an elongated flexible collar structure having opposite ends, upper and lower edges, and a centrally located inner compartment. The inner compartment has an access port therein. A moisture impervious flexible plastic container is located within the compartment, and has a closable access opening therein. A flap appears on the upper edge of the collar structure and normally extends over the access port in the collar structure. Attachment means are located on the ends of the collar structure to secure the ends of the collar structure together.

BRIEF DESCRIPTION OF THE DRAWINGS

FIG. 1 is a frontal prospective view of a person wearing the therapeutic collar of this invention;

FIG. 2 is a side elevational view of FIG. 1 shown at enlarged scale;

FIG. 3 is a rear elevational view of the therapeutic collar;

FIG. 4 is an exploded view of the therapeutic collar of FIG. 3 and the plastic container that draws inside of the collar;

FIG. 5 is an enlarged scale sectional view taken on line 5—5 of FIG. 3;

FIG. 6 is an enlarged scale sectional view taken on line 6—6 of FIG. 4; and

FIG. 7 is an enlarged scale sectional view taken on line 7—7 of FIG. 3.

DESCRIPTION OF THE PREFERRED EMBODIMENT

The collar 10 is of elongated construction and is manufactured of terry cloth or the like which is comfortable when worn around the neck of the person utilizing the invention. Collar 10 has opposite ends 12 and 14, upper and lower edges 16 and 18, respectively, and an elongated flap 20 located along the central portion of the upper edge 16. A printable panel 22 appears on the exterior side of flap 20 when it is folded over the body of collar 10 as shown best in FIG. 3. The panel 12 is adapted to have a slogan 24 or suitable design printed thereon. As best shown in FIG. 4, stitching 26 extends substantially around collar 10, but terminates in a space at the upper edge 16 thereof to create an access port 28 for permitting access to the inner compartment 29 which exists within collar 10.

Male snap components 30 are mounted in end 14 of collar 10, and compatible female snap components 32 are similarly mounted in end 12 of collar 10. The snap components 30 and 32 are secured together, as best shown in FIGS. 1 and 6, to secure the collar 10, around the neck of the person wearing it. Snap components 30 and 32 are the preferred type of fastening component, because a Velcro ® type fastener does not work well in the presence of moisture. The ends 12 and 14 of collar 10 are tapered in opposite directions as shown by end edges 34 and 36 of FIG. 4, to create a uniform V-shaped configuration 38 best shown in FIG. 1. Oppositely tapered ends 40 and 42 of flap 20 are useful in creating the appearance of a typical collar, as best shown in FIG. 1.

A flexible plastic container 44 having a shape compatible to that of interior compartment 29 of collar 10 is adapted to dwell within the interior compartment 29 as best shown in FIGS. 5 and 7. Container 44 has an access opening spout 46 in the central upper portion thereof which has sealing interlock surfaces 48 (of typical construction) to prevent any leakage of any material in the interior compartment 50 of container 44.

The numeral 52 in FIG. 5 designates either coolant material, such as crushed ice, or conventional heat inducing chemical material.

In operation, the flexible plastic container 44 is positioned within interior compartment 29 of collar 10 through access port 28. Suitable heat or coolant material 52 is introduced into the interior compartment 50 of container 44 through the opening spout 46. The spout 46 is then sealed by actuating the interlock surfaces 48, and the spout is folded over the body of the container as best shown in FIG. 7.

The collar is then placed around the neck 54 of the person wearing the device as best shown in FIGS. 1 and 2. The snap components 30 and 32 are thereupon mated as described heretofore, to hold the collar comfortably and securely around the neck 54 of the person wearing the apparatus.

Through the process of conduction, the heat or cold generated by the material 52 passes through the material of container 44 and the material of collar 10 to warm or cool, as the case may be, the neck 54 of the person wearing the apparatus.

The material in plastic container 44 can be replenished as desired by reversing the process discussed heretofore. The flap 20 serves to conceal the access port 28, and serves additionally to provide a suitable printable panel 22 for the creation of slogans 24 or appropriate designs.

The shape of the various components of the collar 10, and in particular, the tapered ends 40 and 42 of flap 20 and the tapered end edges 34 and 36 of collar 10 create an aesthetic and pleasing appearance.

It is thus seen that this invention achieves at least its stated objectives.

I claim:

1. A therapeutic collar, comprising:

an elongated flexible collar means having opposite ends, upper and lower edges, and a single centrally located inner compartment between said opposite ends, said compartment having an access port therein at said upper edge;

a moisture impervious flexible plastic container in said compartment and having a closable access opening therein, adjacent said upper edge of said collar means, said access opening being a flexible spout that is extendable through said access port in said collar means;

a flap on the upper edge of said collar means and normally extending over said access port and folded downwardly therefrom;

said flexible spout folded over and dwelling between said collar means and said flap when said collar is in an in-use condition;

said collar being free from separate insulative components for said flexible plastic container;

and compatible attachment means on the ends of said collar means to secure the ends of said collar means together.

2. The collar of claim 1 wherein said ends of said collar are tapered in opposite directions to create a uniform V-shaped configuration when superimposed over each other.

3. The collar of claim 1 wherein said flexible spout has a width less than the length of said upper edge of said collar means and less than the length of said plastic container.

4. The collar of claim 3 wherein said access port has a width substantially the same as the width of said flexible spout.

* * * * *